United States Patent

Krause et al.

[11] Patent Number: 5,258,163
[45] Date of Patent: * Nov. 2, 1993

[54] TEST CARRIER FOR ANALYSIS OF FLUIDS

[75] Inventors: Manfred Krause, Viernheim; Bernd Klein, Ludwigshafen; Gerhard Schindler, Gründstadt; Peter Schäfer, Ludwigshafen; Siegfried Nötzel, Wilhelmsfeld, all of Fed. Rep. of Germany

[73] Assignee: Boehringer Mannheim GmbH, Mannheim, Fed. Rep. of Germany

[*] Notice: The portion of the term of this patent subsequent to Dec. 22, 2009 has been disclaimed.

[21] Appl. No.: 960,222

[22] Filed: Oct. 13, 1992

Related U.S. Application Data

[63] Continuation of Ser. No. 681,598, Apr. 8, 1991, abandoned.

[30] Foreign Application Priority Data

Apr. 14, 1990 [DE] Fed. Rep. of Germany ....... 4012216

[51] Int. Cl.[5] ............................................. G01N 33/52
[52] U.S. Cl. ......................................... 422/58; 422/56; 422/60; 422/68.1; 435/970; 435/805; 436/170; 436/165
[58] Field of Search ............ 422/55, 56, 58, 60, 61, 102, 104, 68.1; 436/170, 165, 66, 169; 435/805, 970; 206/828, 456

[56] References Cited

U.S. PATENT DOCUMENTS

| | | | |
|---|---|---|---|
| 4,549,655 | 10/1985 | Forsythe, Jr. et al. | 206/569 |
| 4,668,472 | 5/1987 | Sakamoto et al. | 422/56 |
| 4,719,085 | 1/1988 | Jacobs | 422/56 |
| 4,839,297 | 6/1989 | Freitag et al. | 436/170 |
| 4,877,586 | 10/1989 | Devaney, Jr. et al. | 422/101 |
| 4,912,034 | 3/1990 | Kalra et al. | 435/7 |
| 5,173,261 | 12/1992 | Krause et al. | 422/58 |

*Primary Examiner*—James C. Housel
*Assistant Examiner*—Long V. Le
*Attorney, Agent, or Firm*—Nikaido, Marmelstein, Murray & Oram

[57] ABSTRACT

Test carrier for the analysis of fluids with a frame (2) consisting of at least two parts surrounding a test field opening (6) and with a test field disposed in the test field opening (6). In order to provide such a test carrier with frame with which it is possible to assemble the test field out of several test layers manufactured separately from one another, it is proposed that the test field be designed as a test layer package (7) with test layers (10, 11, 12) resting loosely on one another, the frame (2) comprise two shaped pieces of plastics material, one of which serves as base part (4) and comprises a seat (16) for accommodating the test layers (10, 11, 12), while the other serves as lid part (3) and comprises a bearing surface (17) resting on the topmost layer (10) of the test layer package (7). The lid part (3) and the base part (4) are in addition designed with elastic properties so that the pressure with which the bearing surface (17) presses onto the test layer package (7) is substantially constant in the tolerance range of the thickness of the test field package (7).

25 Claims, 3 Drawing Sheets

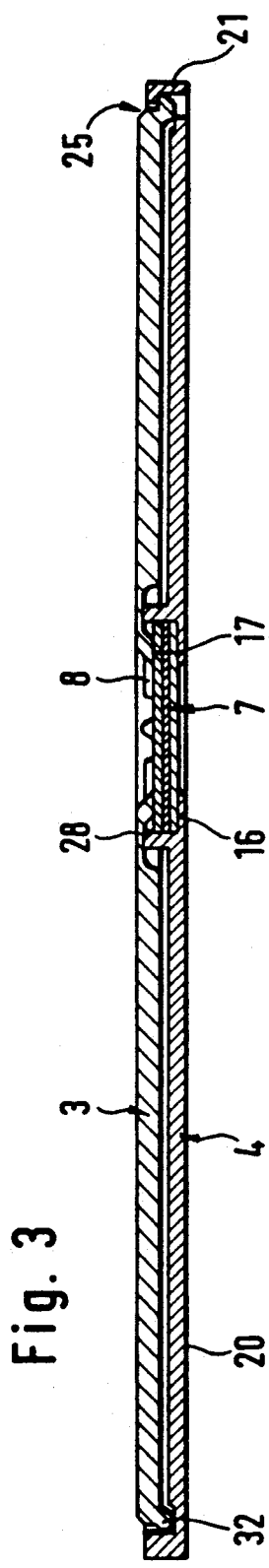
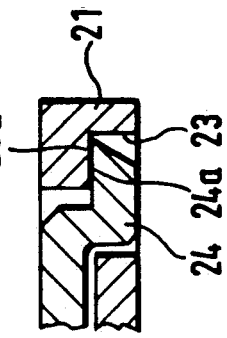
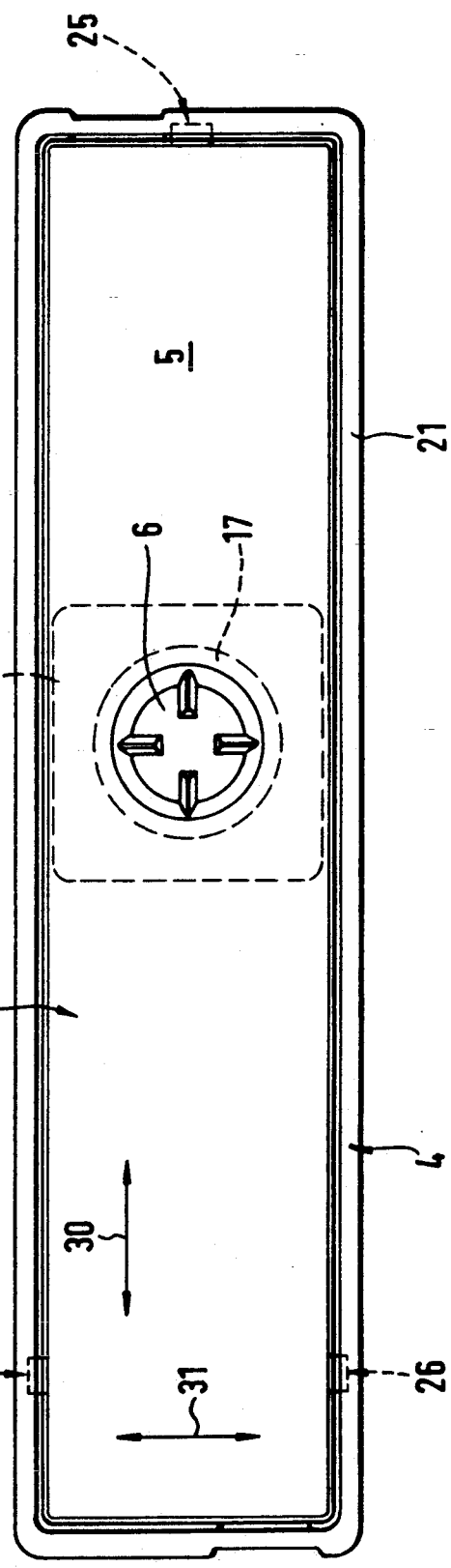

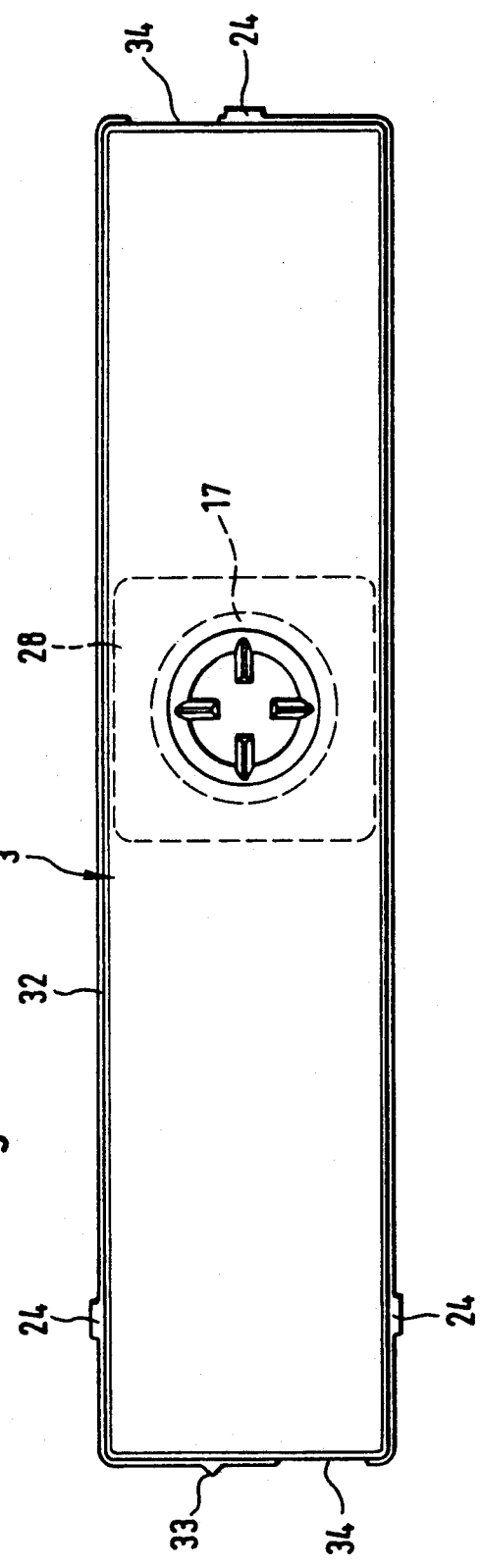
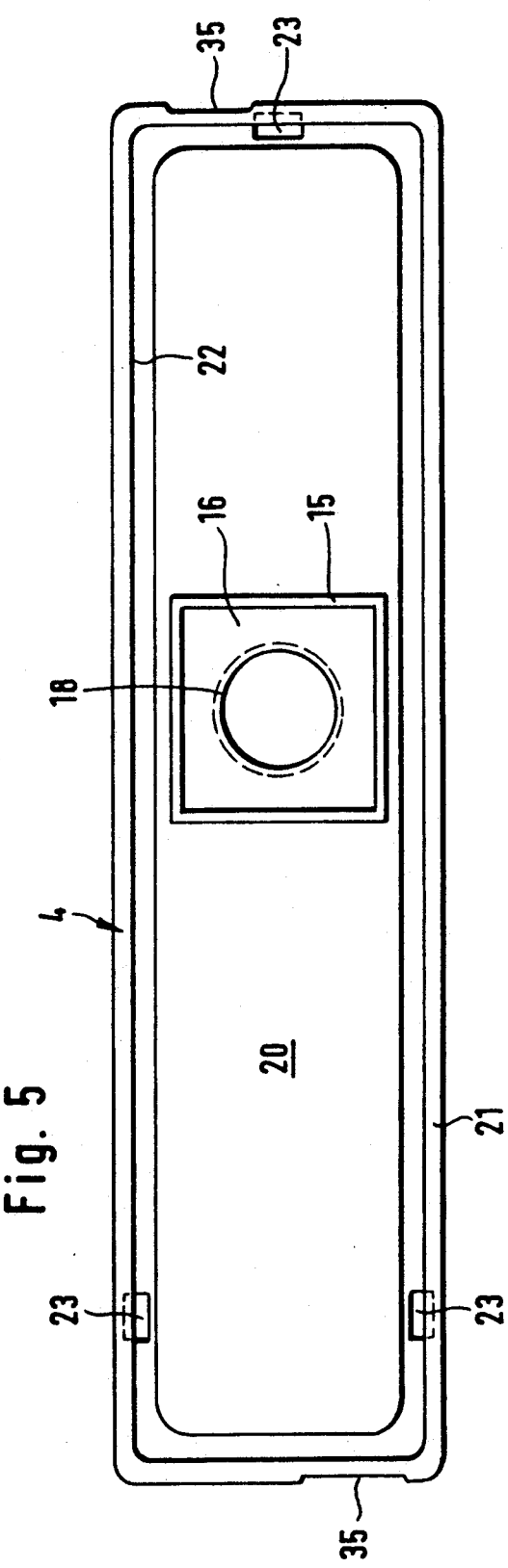

TEST CARRIER FOR ANALYSIS OF FLUIDS

This application is a continuation of application Ser. No. 681,598 filed Apr. 8, 1991, now abandoned.

The invention relates to a test carrier for the analysis of fluids, with a frame consisting of at least two parts surrounding a test field opening and with a test field disposed in the test field opening.

For the qualitative or quantitative analytical determination of constituents of fluids, in particular body fluids of humans or animals, so-called carrier-bound tests are increasingly being used. In these tests, reagents are embedded in the test layers of an analysis element designated overall as a test carrier. They are brought into contact with the sample. The reaction of sample and reagents leads to a detectable signal, in particular a colour change, which can be evaluated visually or by means of an apparatus, in most cases reflection-photometrically. Many different types of test carrier are known, which differ from one another not only with respect to the reagents used, but also in their design, in particular as regards the arrangement and fixing of the test layers. The following two types are of particular practical importance.

Strip-type test carriers consist mainly of an elongated carrying layer of plastics material and test layers attached thereto. The connection between the test layers and the plastics carrier is usually made by bonding, and the bonding in many cases does not take place over the whole surface, but only on one edge of the test layer, or additional fixing means (nets or fixing films) are fixed to the carrying layer, which secure the test layers indirectly. In this way a very wide range of arrangements of the test layers next to one another and/or on one another, according to the requirements of the individual test, is possible. The test layers can be manufactured independently of one another and be joined together at the final assembly of the strip-type test carrier.

The invention is directed towards the type of test carrier mentioned in the preamble, in which a test field is held by a frame in a similar way to a photographic slide. They are referred to below as "test carriers with frames" and in the English-language literature as "analysis slides". The sample is in this case usually placed on the test field through the test field opening. On the conclusion of the test reaction the colour formation—usually on the side of the test field facing away from the sample side—can be observed and/or measured.

With this type of test carrier no test fields consisting of several separate test layers have been used to date. Instead the test field usually consists of a transparent plastics film as carrier, which is coated successively with different layer-forming fluids in which the reagents or auxiliary constituents for the testing are contained. Although this makes a multilayer design possible, the test field consists of a one-piece layered composite whose individual layers are connected to one other over their whole area. This is necessary in order to make easy assembly of the test fields in the frame possible and above all to ensure uniform fluid contact between the individual layers. This uniform fluid contact is a pre-requisite for an accurate analysis, because a non-uniform fluid transfer between the individual test layers results in nonhomogeneous colour formation, which impairs the measuring accuracy considerably. In addition it should be borne in mind that the individual layers must be as thin as possible in order to keep the required amount of sample and reagents as small as possible and at the same time to achieve an intense colour formation.

The need to manufacture the test field, in the case of test carriers with frames, as a one-piece layered composite leads to considerable limitations in the use of this type of test carrier. The development of the layered test composite is very expensive. Its manufacture is also difficult, because the accuracy of the analysis depends on each individual layer being manufactured with very close tolerances in consistent quality. This is naturally more difficult to achieve if the layers are applied successively in the form of a layer-forming fluid than if the test layers are manufactured completely separately from one other and are joined together only at the final assembly of the test carrier. Above all it has proved highly advantageous to combine together test layers of very different structure. Thus, for example, fibre composite structures (fabric or fleece), fine-pored plastics layers ("membranes") and bonded particle structures (e.g. EP-A-0 013 156) each have specific properties which are advantageous for particular applications. In the case of the known test carriers with frames the combined use of such different structures is possible to only a very limited extent.

The object of the invention is therefore to provide a test carrier with frame with which it is possible to assemble the test field from several test layers manufactured separately from one another. It is also naturally intended that the accuracy of the analysis will not be affected and rational manufacture of the test carrier will be possible.

The object is achieved in the case of a test carrier of the kind mentioned in the preamble by the fact that the test field is designed as a test layer package with at least two superimposed test layers not connected to one another over their whole area, the frame has two shaped pieces of plastics material, in which the first shaped piece serves as base part and comprises a seat for the test layers and the second shaped piece serves as lid part and comprises a bearing surface resting on the topmost test layer of the test layer package, and the frame is designed with such elastic properties that the pressure with which the bearing surface presses onto the test layer package is substantially constant in the tolerance range of the thickness of the test field package.

In the context of the present invention it was found that the use of a test layer package with several test layers not connected to one another over their whole area leads in the case of the test carriers with frames known to date to a non-uniform fluid transfer between the test layers and hence to poor analytical accuracy, because the unavoidable, albeit comparatively small thickness tolerances of customary test fields cause a highly varied pressure loading of the test field package. It was found that this problem can be avoided if steps are taken to see that the pressure with which the bearing surface presses onto the test layer package is substantially constant in the tolerance range of the thickness of the test field package. "Substantially constant" must be understood to mean that the pressure constancy and the resulting uniformity of the fluid transfer between the test layers must ensure the desired measuring accuracy. The pressure of the bearing surface onto the test layer package must preferably vary by less than 20% if the thickness of the latter changes by 0.01 mm.

The desired elasticity can be achieved in many different ways. For example, the base part and/or the lid part itself can be made of a sufficiently elastic material, or elastically resilient spring elements (for example a pressure ring of a highly elastic material) can be used.

Particularly preferred embodiments assume, however, that a plastics material with relatively low inherent elasticity is used and the elastic flexibility is achieved by suitable structural design of the lid part and/or base part including their connection elements. In this way a simple design with small dimensions is possible, the hard frame material being preferred because of its handling characteristics, in particular with fully mechanised processing of the test carriers in corresponding automatic analyzers.

Such preferred structural measures and other details of the invention are explained below by means of exemplifying embodiments represented diagrammatically in the figures, where:

FIG. 3 shows a longitudinal section through a test carrier according to the invention, FIG. 4 is an enlarged cutout from FIG. 3, FIG. 5 is a view onto a base part and FIG. 6 is a view onto a lid part, FIG. 7 is a view onto a test carrier according to the invention.

Figure 1:
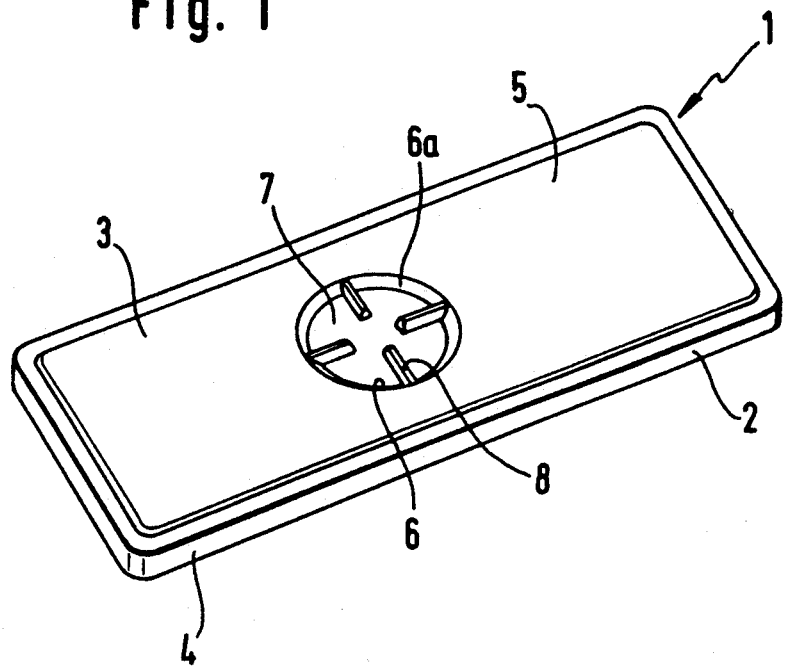
FIG. 1 is a perspective view of a test carrier according to the invention.
Figure 2:
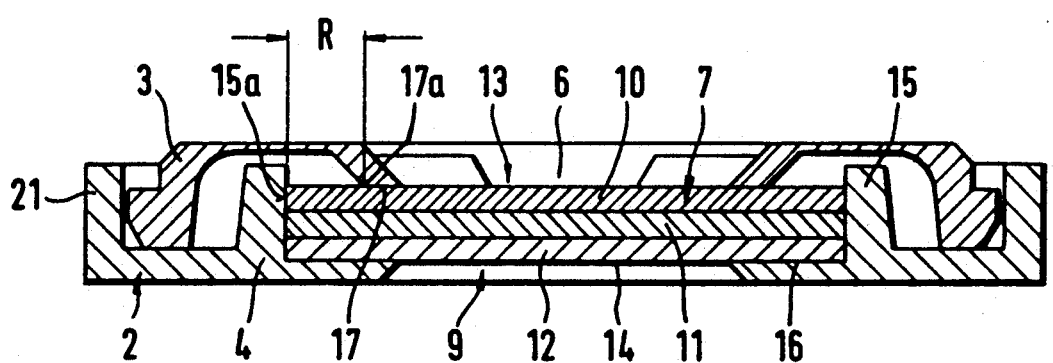
FIG. 2 shows an enlarged cross-section through a test carrier according to the invention.

The test carrier 1 represented in FIG. 1 has a flat frame 2, preferably less than 3 mm, particularly preferably only approx. 2 mm thick, which consists of a lid part 3 and a base part 4. In the centre of the upper frame surface 5 is situated a test field opening 6 through which the test field is visible. Pressure tongues 8 lie flat on the test field, which start from the edge 6a of the test field opening 6.

Details are shown in FIGS. 2 to 7.

The test field is designed as a test layer package 7 consisting of three loosely superimposed test layers 10, 11, 12. They fulfil different functions in the test process. For example, the first test layer 10 can be a covering mesh which protects the layers beneath it and at the same time contains a wetting agent which promotes the spread of the sample. The layer 11 can serve to separate the erythrocytes out of the blood sample. A glass fibre fleece according to U.S. Pat. No. 4,477,575, for example, is suitable. The layer 12 can for example be a reagent film containing a reagent system which leads to a colour change characteristic for the analysis on the underside of the layer 12. Details of the test sequence are not important for the present invention. As a rule, however, the test sequence is such that the sample is fed on one side of the test layer package, which can be designated as the sample feed side 13, and the measurement or visual evaluation of the detection signal takes place on the other side of the test layer package (detection side 14) through a second test field opening 9 which is usually of the same size as the test field opening 6. The layer package has in most cases unavoidable thickness variations, which for example are in the order of magnitude of plus or minus 0.02 mm. On the other hand the layers have to be reliably superimposed over their whole area, so that a uniform transfer of the sample from one layer to the other is achieved. Even relatively small differences in the applied pressure lead, as was recognized in the context of the present invention, to spotty colour formation. It was found that if a rigid frame is used with test carriers whose layers lie at the upper limit of the tolerance range, inadequate passage of the liquid occurs. This can probably be attributed to an interfering compression of individual test layers. If the test package thickness lies at the lower limit of the tolerance range, spotty colour formation is found, from which non-uniform fluid transfer can be concluded.

The layer package 7 lies in a flat seat 16 which is formed in the base part 4. The lid part 3 comprises a bearing surface 17. In the represented case the bearing surface surrounds the test field opening in a ring shape. It can also however be designed in another manner. If for example the opening 6 is to be as large as the test layers 12 or even slightly larger, the bearing surface can be formed only by the underside of pressure tongues projecting into the test field opening. The use of pressure tongues has also proved advantageous inasmuch as the absorption of the sample into the test layer is promoted by capillary gaps between the underside of the pressure tongues and the topmost test layer 10.

The bearing surface 17 rests in any case on the topmost test layer 10 of the test layer package 7. "Top" must be understood here as the side facing towards the lid part. This does not necessarily have to be the sample feed side.

The seat 16 is in the represented case designed as a trough surrounded by an enclosed wall. Other means can however be used for the positioning of the test layer package 7, in particular pegs or wall pieces with intermediate spaces. They are designated overall as the positioning means 15. Between the inner limitation 15a, facing towards the test layer package 7, of the positioning means 15 and the outer limitation 17a of the bearing surface 17 there is preferably provided an annular gap R which is sufficiently large to prevent absorption of the sample fluid by capillary forces into the annular gap R. It is preferably at least 0.1 mm, particularly preferably at least 0.3 mm, wide.

The connection of the lid part 3 to the base part 4 is preferably undertaken by adhesive-free discrete connection elements 25, 26, 27 which are preferably designed so that they comprise limiting elements 23a, 24a (FIG. 4) which butt positively (formlocking) against one another and limit the relative movement perpendicular to the plane of the test layer package 7. In the represented case the lid part 3 has a projection 24, whose upper surface forms one of the limiting elements. The base part 4 has recesses 23, which are open towards the centre of the frame 2 and on which the limiting elements 23a on the base part side are formed. The projections 24 engage with the recesses 23. One projection 24 and one recess 23 respectively form a connection element 25, 26, 27. Different designs of the connection elements are possible, but it is advantageous if they are designed so that on the one hand they limit in a defined manner the relative movement between the lid part and the base part in the direction perpendicular to the test layers 10 to 12, while on the other they permit a slight relative movement of both parts in the direction parallel to the surface of the test layers 10 to 12, which slight relative movement facilitates the elastic deformation of the lid part 3 and base part 4.

The connection elements 25, 26, 27 are preferably designed as clip connections, whereby the positively interlocking parts 23, 24 are slightly distorted elastically during assembly in order to bring them into engagement with one another. The clip connection must be so designed that it cannot work loose during the elastic deformation according to the invention.

In the represented exemplifying embodiment the base part 4 has, compared with its bottom surface 20, a thickened edge profile 21 against which the clip connections 5 are formed.

In view of the desired elasticity of the lid part and base part it is advantageous if both are fixed with comparatively few discrete adhesive-free connection elements with regard to a relative movement perpendicular to the plane of the test field and that these elements are spaced comparatively far apart. Their spacing should preferably be at least three times as large as the diameter of the test field opening 6. In this way sufficient elasticity will be achieved even with a comparatively rigid plastics material. The rectangular form shown for the frame makes a large spacing of the fixing elements possible with a small overall area.

Alternatively or additionally the elasticity with which the bearing surface 17 is pressed against the test field package 7 is ensured by the fact that at least one of the shaped plastics pieces in the vicinity of the test field opening 6 or 9 has a particularly small material thickness. In the preferred exemplifying embodiment shown this applies to an elasticity region 28 shown in dashes in FIGS. 6 and 7. The material thickness here is preferably below 0.3 mm, particularly preferably below 0.2 mm. The elasticity region 28 has a surface area at least as great as the test field opening 6, 9. If these openings are different, the statement refers to the greater of the two test field openings.

For ease of assembly it is in addition advantageous if the positioning means 15 which surrounds the seat 16 in the base part 6 is higher than the test layer package 7. Since this positioning device preferably lies in the elasticity region 28, sufficient space is provided for it despite the small overall height of the frame 2. The high positioning means 15 ensures that the test layers 10, 11, 12 do not fall out despite the unavoidable vibrations occurring during the mechanical assembly.

In practice it is also important that the lid part and base part are positioned accurately relative to one another in the direction of their surface dimensions indicated by the arrows 30 and 31 in FIG. 7. For this purpose the lid part has a narrow peripheral fitting strap 32 which rests against the inner wall 22 of the edge profile 21 of the base part 20. Accuracy of assembly is facilitated by a positioning lug 33.

The lid part 3 and the base part 4 are preferably manufactured by the injection moulding of polystyrene or ABS (acrylonitrile-butadiene-styrene polymer). They are with advantage provided at their edges with resilient recesses 34 and 35, against which the gate pins rest during the manufacturing process.

We claim:

1. A test carrier for analysis of fluids, comprising:

frame means for forming a main body of said test carrier, said frame means comprising two molded pieces of plastic material forming a base part and a lid part of said frame means, each of said base part and said lid part including an aperture forming a test field opening;

seating means disposed on an inner surface of said base part and surrounding said aperture of said base part for seating a plurality of loosely stacked superimposed imperforate test layers therein, said seating means defining a test layer area;

said lid part including attachment means for attaching said lid part to said base part, said lid part having bearing means in said test layer area for resting on a topmost test layer of said superimposed test layers;

said frame means further comprising a plurality of connection means for connecting the lid part and the base part to each other and limiting relative movement thereof in a direction perpendicular to a plane of the superimposed test layers, said connection means including limiting means on each part provided in respective pairs which butt positively against each other, said limiting means for holding said lid part and said base part in a particular position relative to each other, and wherein each of said plurality of connection means is spaced a distance from other connection means which is at least three times as great as a smallest distance between diametrically opposed sides of the apertures;

said frame means having elasticity properties wherein a pressure with which said bearing means presses onto said superimposed test layers to bring said superimposed test layers in uniform fluid contact with each other is substantially constant in a tolerance range of the test layers, wherein uniform fluid contact is ensured between individual test layers and wherein said test layers remain flat and undeformed under said pressure.

2. Test carrier of claim 1, wherein the lid part exerts pressure through the bearing means onto the superimposed test layers, which pressure changes by less than 20% if the thickness of the superimposed test layers changes by 0.01 mm.

3. Test carrier of claim 1, wherein the seating means of the base part is surrounded by a positioning means for positioning the test layers on the seating means, said positioning means being higher than the superimposed test layers.

4. Test carrier of claim 3, wherein the bearing means includes an outer limitation, and the positioning means includes an inner limitation facing toward the superimposed test layers, said outer limitation and said inner limitation defining an annular gap therebetween.

5. A frame type test carrier as recited in claim 1, wherein said frame means has side portions at a periphery of said base part, and said lid part has an outer surface which engages an inner surface of said side portions of said frame means.

6. A frame type test carrier as recited in claim 1, wherein said frame means has side portions at a periphery of said lid part, and said base part has an outer surface which engages an inner surface of said side portions of said frame means.

7. Test carrier of claim 1, wherein the lid part and the base part includes a plurality of connection means for connecting the lid part and the base part to each other and limiting relative movement thereof in a direction perpendicular to a plane of the superimposed test layers.

8. Test carrier of claim 1, wherein the connection means includes limiting means on each part provided in respective pairs which butt positively against each other, said limiting means for holding said lid part and said base part in a particular position relative to each other.

9. Test carrier of claim 1, wherein each pair of limiting means forms a clip connection.

10. Test carrier of claim 9, wherein at least one of the lid part and the base part has an edge portion which protrudes from a surface of that part, said edge portion protruding around a perimeter of that part, wherein the clip connection engages with the edge portion.

11. A test carrier for analysis of fluids, comprising:
frame means for forming a main body of said test carrier, said frame means comprising two molded pieces of plastic material forming a base part and a lid part of said frame means, and each including an aperture, said apertures forming a test field opening;
seating means disposed on an inner surface of said base part and surrounding said aperture of said base part for seating a plurality of loosely stacked superimposed imperforate test layers therein, said seating means defining a test layer area;
said lid part including attachment means for attaching said lid part to said base part, said lid part having bearing means in said test layer area for resting on a topmost test layer of said superimposed test layers; wherein at least one of said base part and said lid part includes an elasticity region which is thinner than a substantial remainder of the at least one part, a surface area of the elasticity region being at least as great as the apertures and a thickness of the elasticity region being less than 0.3 mm;
said frame means having elasticity properties wherein a pressure with which said bearing means presses onto said superimposed test layers to bring said superimposed test layers in uniform fluid contact with each other is substantially constant in a tolerance range of the test layers, wherein uniform fluid contact is ensured between individual test layers, wherein said test layers remain flat and undeformed under said pressure.

12. Test carrier of claim 11, wherein the lid part and the base part includes a plurality of connection means for connecting the lid part and the base part to each other and limiting relative movement thereof in a direction perpendicular to a plane of the superimposed test layers.

13. Test carrier of claim 12, wherein the connection means includes limiting means on each part provided in respective pairs which butt positively against each other, said limiting means for holding said lid part and said base part in a particular position relative to each other.

14. Test carrier of claim 13, wherein each pair of limiting means forms a clip connection.

15. Test carrier of claim 14, wherein at least one of the lid part and the base part has an edge portion which protrudes from a surface of that part, said edge portion protruding around a perimeter of that part, wherein the clip connection engages with the edge portion.

16. Test carrier of claim 11, wherein the elasticity region thickness is less than 0.2 mm.

17. Test carrier of claim 11, wherein the lid part exerts pressure through the bearing means onto the superimposed test layers, which pressure changes by less than 20% if the thickness of the superimposed test layers changes by 0.01 mm.

18. Test carrier of claim 11, wherein the seating means of the base part is surrounded by a positioning means for positioning the test layers on the seating means, said positioning means being higher than the superimposed test layers.

19. Test carrier of claim 18, wherein the bearing means includes an outer limitation, and the positioning means includes an inner limitation facing toward the superimposed test layers, said outer limitation and said inner limitation defining an annular gap therebetween.

20. A frame type test carrier as recited in claim 11, wherein said frame means has side portions at a periphery of said base part, and said lid part has an outer surface which engages an inner surface of said portions of said frame means.

21. A frame type test carrier as recited in claim 11, wherein said frame means has side portions at a periphery of said lid part, and said base part has an outer surface which engages an inner surface of said side portions of said frame means.

22. A test carrier for analysis of fluids, comprising:
frame means for forming a frame body of the test carrier, said frame means comprising two molded pieces of plastic material forming a base part and a lid part of said frame means, and each including an aperture, said apertures forming a test field opening;
seating means disposed on an inner surface of said base part and surrounding said aperture of said base part for seating a plurality of superimposed test layers therein, said seating means defining a test layer area;
said lid part including attachment means for attaching said lid part to said base part, said lid part further including bearing means in said test layer area for resting on a topmost test layer of said superimposed test layers, the bearing means comprising a plurality of bearing tongues which project into the test field opening, said bearing tongues resting on said topmost layer.

23. A test carrier for analysis of fluids, comprising a test layer package of at least two imperforate superimposed contacting test layers,
a frame having first and second molded plastic pieces, wherein the first plastic piece is a base part which includes a seat for the test layers, and wherein the second plastic piece is a lid part which includes a bearing surface resting on the test layer furthest from the seat,
said frame having flexible means located thereupon for causing the bearing surface to press upon the test layer package with a pressure which is substantially constant over a tolerance range of the thickness of the test layer package, said flexible means being formed by an area of said frame having increased flexibility relative to a substantial remainder of said frame, wherein said bearing surface presses upon said test layer package upon engagement of said base part and said lid part, and wherein said test layers remain flat and undeformed upon said engagement.

24. A test carrier for the analysis of fluids comprising:
a frame consisting of at least two parts, each of said parts having an aperture therein, said apertures forming a test field opening, and,
a test field disposed in the test field opening,
the test field forming at est layer package with at least two imperforate superimposed test layers not connected to one another over their whole area,
said at least two parts each comprising a molded piece of plastic material, wherein
a first molded piece serves as base part and comprises a seat for the test layers, and the second molded piece serves as a lid part and comprises a bearing surface resting on a topmost test layer of the test layer package, the frame having elastic properties wherein a pressure with which said bearing surface presses onto the test layer package is substantially constant in a tolerance range of the test layer package, and wherein said test layers remain flat and undeformed under said pressure.

25. A test carrier for analysis of fluids comprising:

frame means for forming a main body of said test carrier, said frame means comprising two molded pieces of plastic material forming a base part and a lid part of said frame means, and each including an aperture, said apertures forming a test field opening;

seating means disposed on an inner surface of said base part and surrounding said aperture of said base part for seating a plurality of loosely stacked superimposed imperforate test layers therein, said seating means defining a test layer area;

said lid part including attachment means for attaching said lid part to said base part, said lid part having bearing means in said test layer area for resting on a topmost test layer of said superimposed test layers;

said frame means having elasticity properties wherein a pressure with which said bearing means presses onto said superimposed test layers to bring said superimposed test layers in uniform fluid contact with each other is substantially constant in a tolerance range of the test layers, wherein said fluids can penetrate through an entire horizontal dimension of said test layers, wherein said test layers remain flat and undeformed under said pressure.

* * * * *